United States Patent [19]

Wiker et al.

[11] 4,149,278
[45] Apr. 17, 1979

[54] COMPACT ARTIFICIAL HAND

[76] Inventors: Robert A. Frosch, Administrator of the National Aeronautics and Space Administration, with respect to an invention of Gordon A. Wiker; Wolfgang A. Mann, both of Arcadia, Calif.

[21] Appl. No.: 837,259

[22] Filed: Sep. 27, 1977

[51] Int. Cl.² .......................... A61F 1/06; B25J 3/00
[52] U.S. Cl. ........................................... 3/12.5; 3/1.1; 414/6
[58] Field of Search ................. 3/1.1, 12, 12.1, 12.4, 3/12.5; 214/1 CM, DIG. 2

[56] References Cited

U.S. PATENT DOCUMENTS

| | | | |
|---|---|---|---|
| 2,557,792 | 6/1951 | Maguth | 3/12 |
| 2,640,994 | 6/1953 | Alderson | 3/1.1 |
| 2,701,370 | 2/1955 | Alderson | 3/1.1 |
| 3,007,176 | 11/1961 | Hafner | 3/1.2 |
| 3,043,448 | 7/1962 | Melton | 214/1 CM |
| 3,066,805 | 12/1962 | Sullivan | 214/1 CM |
| 3,155,240 | 11/1964 | Eude et al. | 214/1 CM |
| 3,202,449 | 8/1965 | Lemelson | 294/88 |
| 3,451,224 | 6/1969 | Colechia et al. | 214/1 CM X |
| 3,952,880 | 4/1976 | Hill et al. | 214/1 CM |
| 4,068,763 | 1/1978 | Fletcher et al. | 3/12.5 X |

FOREIGN PATENT DOCUMENTS

| | | | |
|---|---|---|---|
| 2619336 | 11/1976 | Fed. Rep. of Germany | 214/1 CM |
| 1197155 | 7/1970 | United Kingdom | 3/1.1 |
| 512048 | 6/1976 | U.S.S.R. | 214/1 CM |

Primary Examiner—Clifford D. Crowder
Attorney, Agent, or Firm—Monte F. Mott; John R. Manning; Wilfred Grifka

[57] ABSTRACT

A compact and relatively simple artificial hand, which includes hooks pivotally mounted on a first frame to move together and apart, the first frame being rotatably mounted on a second frame to enable "turning at the wrist" movement without limitation, and the second frame being pivotally mounted on a third frame to permit "flexing at the wrist" movement. A hook-driving motor is fixed to the second frame but has a shaft that drives a speed reducer on the first frame which, in turn, drives the hooks. A second motor mounted on the second frame, turns a gear on the first frame to rotate the first frame and the hooks thereon. A third motor mounted on the third frame, turns a gear on a second frame to pivot it.

2 Claims, 6 Drawing Figures

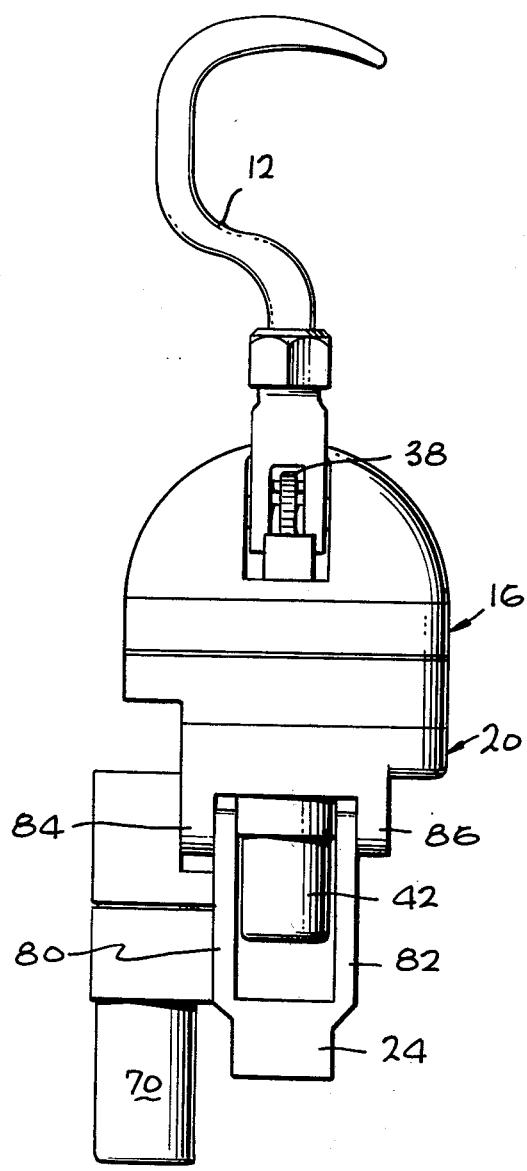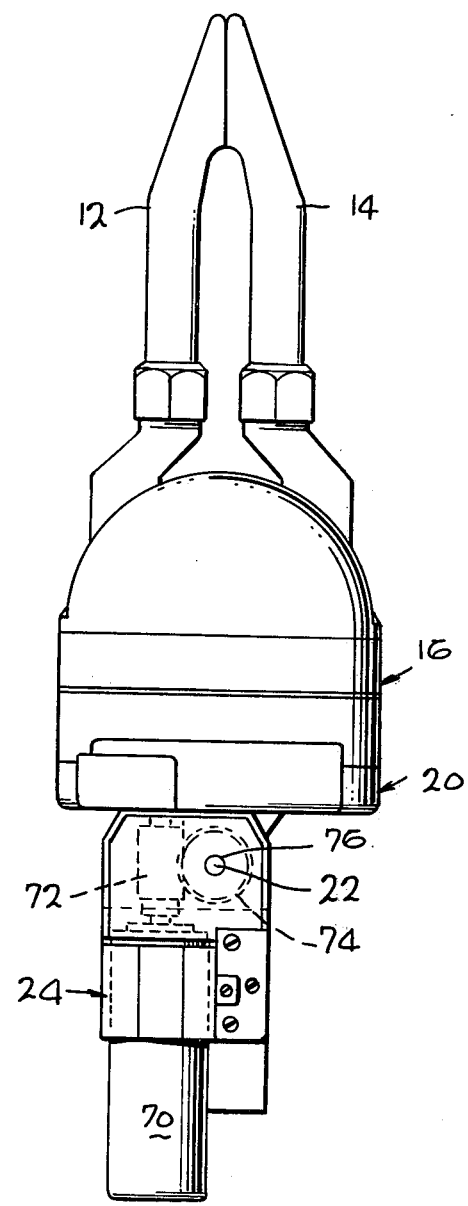
FIG. 2
FIG. 4

COMPACT ARTIFICIAL HAND

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to artificial hand mechanisms.

Artificial hands can be utilized not only as prosthetic devices but also to enable unmanned manipulation as on unmanned space vechicles or in radioactive areas. Where such hands are to have a plurality of degrees of freedom of movement, such as turning without restriction at the "wrist" and flexing at the wrist, the prior art mechanisms show only complex and large drive devices. For exampe, U.S. Pat. No. 2,640,994 shows an artificial hand which can turn at the wrist as well as pivot, but which utilizes a complex and bulky gear train for coupling a motor located far above the wrist to drives that move the fingers, flex the hand at the wrist, and turn the hand at the wrist.

SUMMARY OF THE INVENTION

In accordance with one embodiment of the present invention, an artificial hand is provided which is compact and of relatively simple construction, and yet which has large versatility. The hand includes a first frame which pivotally supports a pair of object-engaging members that pivot together and apart, a second frame which rotatably supports the first one in "pivoting at the wrist" movement, and a third frame which pivotally supports the first one in "flexing at the wrist" movement. A first motor for driving the object-engaging members together and apart, is fixed to the second frame and has a shaft extending along the axis of rotation of the first frame on the second, to drive a gear train on the first frame which moves the members. A second motor fixed to the second frame, drives a worm gear on the first frame that is coaxial with the axis of the first motor shaft, to rotate the first frame in "turning at the wrist" movement. A third motor fixed to the third frame, drives a worm gear on the second frame to pivot the second frame. All three motors can be energized by flexible wires that connect directly to the motors to accommodate only limited "flexing at the wrist" which is undergone by the second frame.

The novel features of the invention are set forth with particularity in the appended claims. The invention will best be understood from the following description when read in conjunction with the accompanying drawings.

BRIEF DESCRIPTION OF THE DRAWINGS

FIG. 2 is a left side elevation view of the hand of FIG. 1.

FIG. 4 is a partial front elevation view of the hand of FIG. 1.

DESCRIPTION OF THE PREFERRED EMBODIMENT

Figure 1:
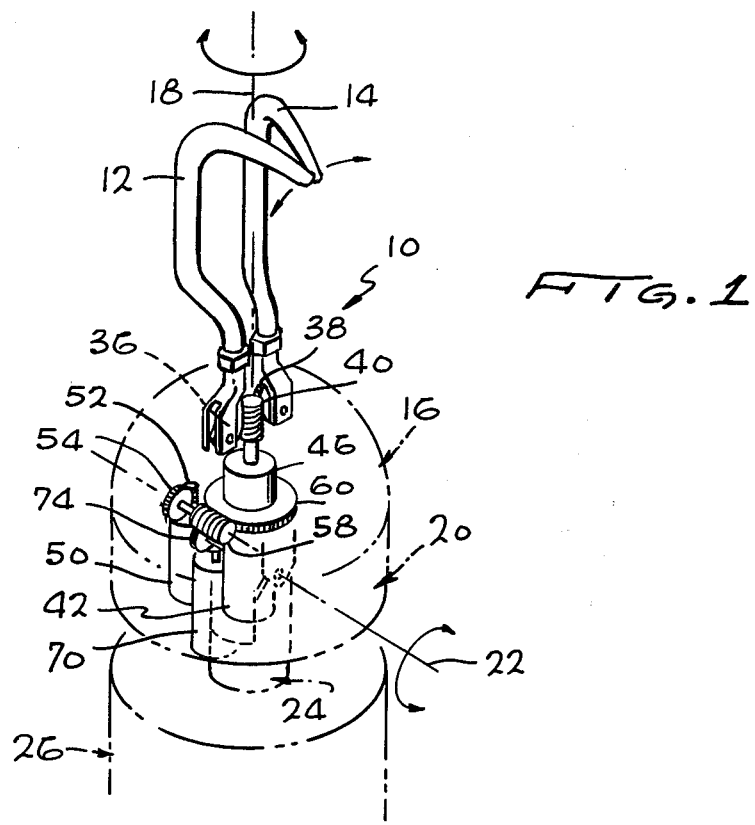
FIG. 1 is a simplified perspective view of an artificial hand constructed in accordance with the invention.

FIG. 1 illustrates an artificial hand 10 which includes a pair of object-engaging members, or hook members 12, 14 which can move apart (up to 70° apart) and together to grasp objects, the hook members being pivotally mounted on a first frame 16. The first frame 16 is rotatably mounted about a longitudinal axis 18 on a second frame 20, to permit movement simulating pivoting of a hand about the wrist, but with the first frame 16 being rotatable by an unlimited number of turns. The second frame 20 is, in turn, pivotable about a lateral axis 22 with respect to a third frame 24 to permit a motion simulating flexing, or up and down movement, of a hand with respect to the forearm. The third frame 24 can be fixed to a support 26, that may be a controllable rod when the artificial hand is utilized where a man cannot be present, or that may be a forearm where the artificial hand is utilized as a prosthetic device.

Figure 5:
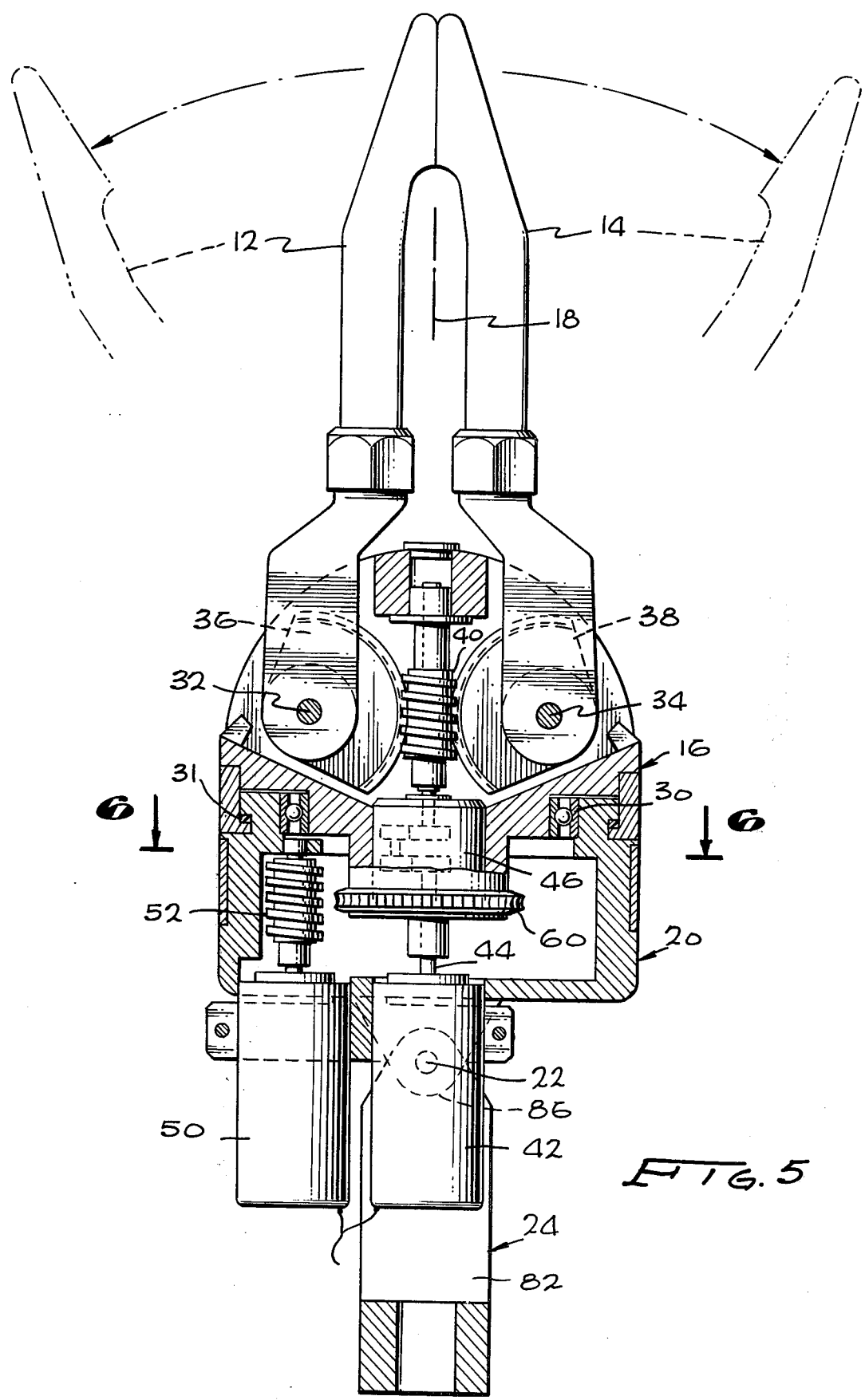
FIG. 5 is a sectional front view of the hand of FIG. 4.

As shown in FIG. 5, the first frame 16 is rotatably supported by a bearing 30 and a Teflon bushing 31 on the second frame 20. The two hook members 12, 14 are pivotally mounted about axes 32, 34 and are fixed to gear segments 36, 38. The gear segments are portions of worm gears, and are engaged with a worm 40. The worm 40 is driven by a reversible motor 42 which is mounted on the second frame 20, so that the motor 42 does not rotate about the axis 18 when the first frame 16 and the hook members thereon rotate. The shaft 44 of the first motor 42 is coaxial with the longitudinal axis of rotation 18, and is coupled to a speed reducer 46 which is fixed to the first frame 16 and which drives the worm 40.

The fact that the motor shaft 44 is coaxial with the axis of rotation 18 of the first frame, means that the first frame can rotate even though the motor 42 is fixed to the second frame. The fact that a worm 40 drives the gear segments fixed to the hook members, means that the hook members are "locked" to any position to which they are pivoted, so that they can be held in that position without continuing energization of the motor 42. The fact that the speed reducer 46 is mounted on the first frame 16 to pivot with the worm 40, means that when the first frame 16 is rotated about the axis 18, only a very small retarding torque is applied by the de-energized first motor 42. If the speed reducer were mounted on the second frame 20, then it would apply considerable retarding torque to the worm 40 when the worm and first frame rotated, and this retarding torque could cause rotation of the worm which could cause the hook members to move apart or together. Of course, the fact that the first motor 42 is not mounted on the first frame 16, means that simple wires can be connected to it, even though the first frame 16 may rotate many revolutions about the axis 18.

Figure 6:
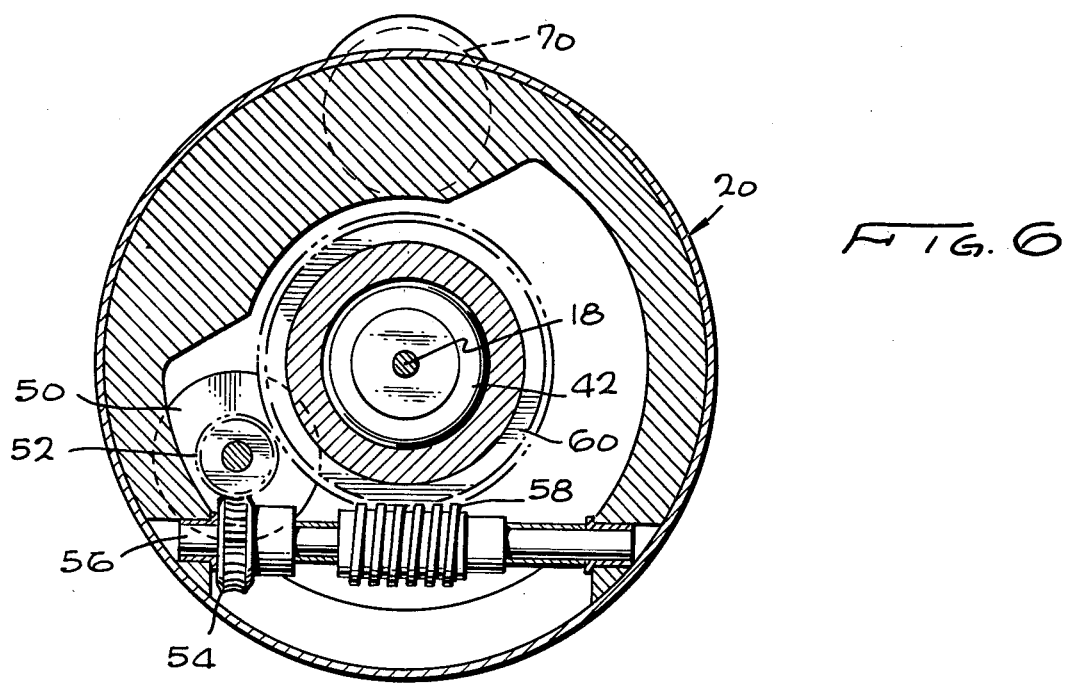
FIG. 6 is a view taken on the line 6—6 of FIG. 5.

The mechanism for turning the first frame 16 with repsect to the second frame 20, includes a second motor 50 which is fixed to the second frame 20. As shown in FIG. 6, the second motor 50 drives a worm 52 that drives a worm wheel 54. The worm wheel 54 turns a shaft 56 to which another worm 58 is fixed. The worm 58 drives a worm wheel 60 that is fixed to the first frame 16, as shown in FIG. 5. The worm wheel 60 surrounds and is coaxial with the first motor shaft 44 and the output shaft of speed reducer 46. When the motor 50 is energized, it turns the worm wheel 60 to slowly rotate the first frame 16, the direction of motor energization determining the direction of first frame rotation.

Figure 3:
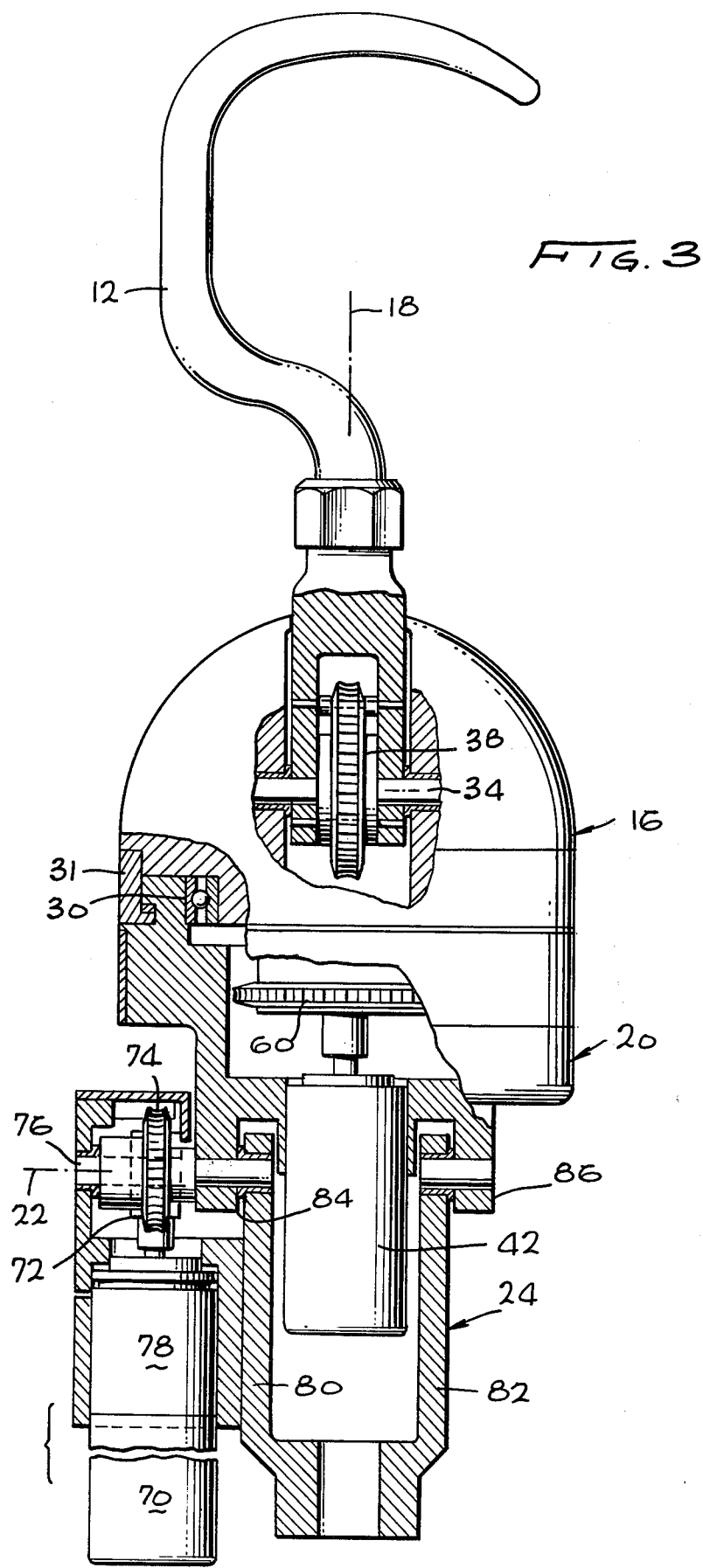
FIG. 3 is a partially sectional side view of the hand of FIG. 2.

As mentioned above, the second frame 20 can pivot about the lateral axis 22 to simulate flexing of a hand with respect to the forearm up to 90° to either side. As shown in FIGS. 3 and 4, pivoting about the axis 22 is accomplished by the third motor 70 which is fixed to the third frame 24, and which drives a worm 72. The worm 72 is engaged with a worm wheel 74 that is fixed to a shaft 76 that is, in turn, fixed to the second frame 20. Thus, when the motor 70 with a gear box portion 78 is energized, it turns the second frame 20 about the axis 22 to cause the second frame to pivot in a motion simulating flexing of a hand with respect to the forearm. Of course, during such pivoting about the axis 22, the hook members 12, 14 may be turned to any direction with respect to the axis 22.

The three motors 42, 50 and 70 are high efficiency miniature types which are typically elongated along the axis of rotation of the motor shaft. All three of the motors are oriented with their axes parallel to axis 18 about which the first frame rotates on the second one, to limit the width of the artificial hand. As shown in FIG. 2, the first motor 42 is located between the arms 80, 82 of a yoke of the third frame 24. The second frame 20 has a pair of arms 84, 86 that lie outside the yoke arms 80, 82 to leave space for the motor 42.

Thus, the invention provides an artificial hand which is compact and of relatively simple construction. This is accomplished by utilizing three frames, the first frame pivotally supporting a pair of hook members and being rotatable without limit on the second frame, the second frame supporting a first motor that pivots the hook members and a second motor that rotates the first frame on the second, and with the second frame being pivotable on the third frame. The mounting of the hook-pivoting motor on the second frame with its shaft coaxial with the axis of rotation of the first frame on the second, and with the speed reducer which is driven by the first motor mounted on the first frame, results in free rotation of the first frame on the second without significant drag from the first motor. In addition, the first motor does not have to rotate without limit and therefore flexible wires can be utilized to supply current thereto. By mounting the motors close to the elements they drive, complex gearing arrangements are avoided, and yet close control of movements of the arm are effected.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An artificial hand device comprising:
   a first frame;
   a second frame rotatably supporting said first frame for rotation about a predetermined axis;
   means for rotating said first frame about said axis;
   a pair of object-engaging members having inner ends pivotally mounted on said first frame;
   a motor mounted on said second frame, said motor having a motor shaft extending along said axis; and
   a speed reducer gear train connected to said motor shaft, said gear train connected to said object-engaging members to pivot them;
   said gear train mounted on said first frame, whereby the motor applies minimum torque tending to retard rotation of the first frame.

2. The device described in claim 1 including:
   a third frame pivotally supporting said second frame for pivoting about a second axis extending substantially perpendicular to said first axis, said third frame comprising a yoke having a pair of arms and said second frame having a pair of arms lying on opposite sides of said yoke arms and pivotally connected thereto, and said first motor lying between said arms of said yoke.

* * * * *